United States Patent [19]
Galzigna et al.

[11] Patent Number: 4,916,220
[45] Date of Patent: Apr. 10, 1990

[54] PALMITOYL-FRUCTOSE-1,6-DIPHOSPHATE, ITS THERAPEUTIC USE AND RELEVANT PREPARATION METHODS

[75] Inventors: Lauro Galzigna, Padova; Franco Gritti, Rome, both of Italy

[73] Assignee: Biomedica Foscama Industria Chimico-Farmaceutica, Rome, Italy

[21] Appl. No.: 340,054

[22] Filed: Apr. 18, 1989

[30] Foreign Application Priority Data

Apr. 19, 1988 [IT] Italy ................................ 20245 A/88

[51] Int. Cl.⁴ ..................... C07H 11/04; C07G 17/00; A61K 31/70
[52] U.S. Cl. ................................... 536/117; 536/124; 514/811
[58] Field of Search .................. 536/117, 124; 514/23, 514/811

[56] References Cited

U.S. PATENT DOCUMENTS

| 4,546,095 | 10/1985 | Markov ................................. 536/117 |
| 4,575,549 | 3/1986 | Diana et al. .......................... 536/117 |

*Primary Examiner*—Ronald W. Griffin
*Assistant Examiner*—Everett White
*Attorney, Agent, or Firm*—Notaro & Michalos

[57] ABSTRACT

A pharmaceutical preparation containing a carrier with palmitoyl-fructose-1,6- diphosphate as the active drug, for use in the therapy of hypophosphatemias, of cardiopathies, and of alcoholism and relevant methods for producing said preparation.

4 Claims, No Drawings

PALMITOYL-FRUCTOSE-1,6-DIPHOSPHATE, ITS THERAPEUTIC USE AND RELEVANT PREPARATION METHODS

The invention relates to the therapeutic use of palmitoyl-fructose-1,6-diphosphate, the relevant methods for preparing it and the pharmaceutical compounds containing said preparation.

The properties of fructose-1,6-diphosphate (FDP), largely used in the therapeutic field for various applications, are well known.

The purpose of the present invention is to obtain a compound having characteristics of absorbability and pharmacological activity higher than those of FDP.

Several carried out experimentations led to the chemical modification of the FDP molecule in order to obtain a phospholipid, namely the fructose-1,6-diphosphate (FDP) in which the introduced function has no toxicity problems because it is actively bio-transformed.

DPF can be prepared either via synthesis in the homogeneous phase or via synthesis in the solid phase.

A. SYNTHESIS IN THE HOMOGENEOUS PHASE

D(+)-fructose-1,6-diphosphate sodium salt (FDP) in the form of lyophilized powder is kept under vacuum in the presence of $P_2O_5$ until constant weight. Starting from crystalline sodium salts of FDP, they are dried in the same way, after trituration.

0.5 dry FDP are treated with 3 ml anhydrous pyridine and dropwise, with 1 ml palmitoyl chloride at 25° C. under strong stirring. After at least 6 hours' stirring, 2 ml of methanol are added. Stirring is continued for 2 further hours and finally 40 ml acetone are added. Palmitoyl-FDP (DPF) precipitates as a white solid which is separated by contrifugation, is washed three times with acetone and dried in a stove under vacuum, at 40° C.

Final yield: 0.6 g.

Traces of pyridine are removed from DPF by re-dissolving it in water and lyophilizing it.

Chromatography on Whatman paper No. 1, with eluent $NH_4Cl$ 3% in water, at 20° C. The chromatogram is dried and revealed with ammonium molybdate and stannous chloride according to Seiler (2). DPF has a Rf of 1.0.

B. SYNTHESIS IN THE SOLID PHASE 0.5 g FDP sodium salt are dissolved in 30 ml water. The solution, cooled in an ice bath, is treated with 5 g of Bio-Rad AG 1×8 resin (or the equivalent) in the form of a free quanternary ammonium base and the suspension is stirred for 3 min. The FDP bound to the resin is quickly collected by filtration on a glass porous medium, washed with water, methanol and ethyl ether.

The resin-bound FDP is in the form of a dry powder which is suspended in 10 ml dichloromethane containing 1.5 g palmitic anhydride. The suspension is stirred for at least 8 hours and then the solid phase is prepared by filtration on a porous medium and washed with dichloromethane, methanol and dichloromethane, in succession, DPF is then removed from the resin by treating the latter with 10 ml formic acid containing 20% trifluoroacetic acid. The resin is separated by filtration on porous medium and the liquid phase is evaporated at reduced pressure and at temperature not over 40° C.

The resin is further dried under vacuum in the presence of NaOH (pellets) and then dissolved in 40 ml water.

After bringing the solution to pH 8 with $NH_4OH$, the same ia lyophilized.

Yield: 0.3 g DPF

The chromatography characteristics on paper and in gas-mass, the elemental analysis and the dosage of the total phosphate according to Martin and Doty (3) document palmitoylation of the starting FDP.

The activity "in vitro" and "in vivo" of the compound was tested and compared with that of FDP.

Small slices of rat heart were used to study comparatively the attack of $^{14}C$-FDP and $^{14}C$-DPF, the latter obtained by palmitoylation of a mixture of "hot" and "cold" FDP.

The results are reported in Table 1.

TABLE 1

Attack of $^{14}C$-FDP and $^{14}C$-DPF to small slices of rat heart.
40 min incubation at 25° C.
FDP (5 mM) 260 ± 20 nmoles/100 mg (3 tests average)
DPF (5 mM) 344 ± 16

DPF has a membrane affinity 30% higher than that of FDP.

The effect on the entrance of $^{45}Ca$ in small slices of heart incubated for 3 min. at 25° C. with 0.5 mM Ca is inhibitory both with FDP and with DPF and therefore both seem to protect the tissue from the anoxy occurring with the entrance of Ca. While FDP has $IC_{50}$ of 8 mM, DPF has a $IC_{50}$ of 5.5. mM and therefore the latter is more active than FDP.

The action of FDP on perfused rat heart is biphasic, i.e. inotropic and chronotropic, positive at concentrations lower than 1 mM (final) and negative for higher concentrations. Also DPF has a biphasic effect but its effect appears at lower doses: $ED_{50}$ of FDP is in fact 0.1 mM while that of DPF is 0.04 mM.

The administration to rats of $^{14}C$-FDP and $^{14}C$-DPF per os (3,000,000 dpm total) allowed measurement of the radioactivity accumulated 1 hour after administration at the level of the organs and the results are reported in Table 2.

TABLE 2

| Accumulation of radioactivity after administration per os. | | |
|---|---|---|
| Heart | Kidneys | Liver |
| FDP 508 | 395 | 624 |
| DPF 1620 | 1324 | 1434 |

We claim:

1. Pharmaceutical preparations containing a carrier with palmitoyl-fructose-1,6-diphosphate as active drug, for use in the therapy of hypophosphatemias, of cardiopathies, and of alcoholism.

2. A process for preparing palmitoyl-fructose-1,6-diphosphate, wherein dry fructose-1,6-diphosphate sodium salt is treated with anhydrous pyridine and palmitoyl chloride and, after stirring, methanol and subsequently acetone are added and the solid precipitate is separated, washed with acetone and dried.

3. A process for preparing palmitoyl-fructose-1,6-diphosphate according to claim 2, wherein palmitoyl-fructose-1,6-diphosphate is cleared from the traces of pyridine by re-dissolving it in water and lyophilizing it.

4. A process for preparing palmitoyl-fructose-1,6-diphosphate, wherein a cooled aqueous solution of fructose-1,6-diphosphate sodium salt is treated with resin in the form of quaternary ammonium free base, the fructose-1,6-diphosphate bound to the resin is collected, suspended in dichloromethane containing palmitic anhydride and, after separation of the solid phase, is treated with formic acid containing 20% trifluoroacetic acid to separate palmitoyl fructose-1,6-diphosphate from the resin.

* * * * *